(12) United States Patent
Cohen et al.

(10) Patent No.: US 9,833,167 B2
(45) Date of Patent: Dec. 5, 2017

(54) METHOD AND SYSTEM FOR SUPERIMPOSING VIRTUAL ANATOMICAL LANDMARKS ON AN IMAGE

(75) Inventors: Amit Cohen, Binyamina (IL); Gera Strommer, Haifa (IL); Uzi Eichler, Haifa (IL)

(73) Assignee: MediGuide Ltd., Haifa (IL)

( * ) Notice: Subject to any disclaimer, the term of this patent is extended or adjusted under 35 U.S.C. 154(b) by 1099 days.

(21) Appl. No.: 12/941,514

(22) Filed: Nov. 8, 2010

(65) Prior Publication Data

US 2011/0054308 A1    Mar. 3, 2011

Related U.S. Application Data

(63) Continuation-in-part of application No. 11/233,420, filed on Sep. 16, 2005, now Pat. No. 8,442,618, which
(Continued)

(51) Int. Cl.
*A61B 5/05* (2006.01)
*A61B 5/06* (2006.01)
(Continued)

(52) U.S. Cl.
CPC ............... *A61B 5/06* (2013.01); *A61B 5/062* (2013.01); *A61B 5/706* (2013.01); *A61B 5/7475* (2013.01);
(Continued)

(58) Field of Classification Search
None
See application file for complete search history.

(56) References Cited

U.S. PATENT DOCUMENTS 3,937,066 A    2/1976  Green et al.
3,974,826 A    8/1976  Eggleton et al.
(Continued)

FOREIGN PATENT DOCUMENTS

EP    0894473    2/1999
EP    1088515    4/2001
(Continued)

OTHER PUBLICATIONS

Panza, Julio A. "Real-time three-dimensional echocardiography: An overview", *The International Journal of Cardiovascular Imaging* 17:227-235, 2001.
(Continued)

*Primary Examiner* — Joseph M Santos Rodriguez
(74) *Attorney, Agent, or Firm* — Dykema Gossett PLLC

(57) ABSTRACT

A system for superimposing virtual anatomical landmarks on an image includes a medical positioning system (MPS) for producing location readings with respect to points within a region of interest in accordance with an output of a location sensor disposed in a medical device. A coordinate system of the MPS is registered with an image coordinate system. A control unit receives a signal from a user to record a location reading when the medical device is at a desired point in the region of interest where the user desires to place a virtual landmark, modifies the recorded location reading for motion compensation, transforms the motion-compensated location reading from the MPS coordinate system to the image coordinate system to produce a target location, and then superimposes a representation of the virtual landmark on the image at the target location.

21 Claims, 6 Drawing Sheets

Related U.S. Application Data is a continuation-in-part of application No. 10/986,567, filed on Nov. 10, 2004, now Pat. No. 9,572,519, which is a continuation-in-part of application No. 10/938,395, filed on Sep. 9, 2004, now Pat. No. 7,778,688.

(51) Int. Cl.

| | | |
|---|---|---|
| *A61B 5/00* | (2006.01) | |
| *A61B 6/04* | (2006.01) | |
| *A61B 6/12* | (2006.01) | |
| *A61B 8/08* | (2006.01) | |
| *A61B 8/12* | (2006.01) | |
| *A61B 8/00* | (2006.01) | |
| A61B 5/01 | (2006.01) | |
| A61B 5/0456 | (2006.01) | |
| A61B 6/00 | (2006.01) | |
| A61B 17/00 | (2006.01) | |
| A61B 34/20 | (2016.01) | |
| A61B 90/00 | (2016.01) | |
| A61B 34/10 | (2016.01) | |

(52) U.S. Cl.
CPC ............. *A61B 6/0492* (2013.01); *A61B 6/12* (2013.01); *A61B 6/465* (2013.01); *A61B 6/466* (2013.01); *A61B 6/469* (2013.01); *A61B 6/5247* (2013.01); *A61B 8/0833* (2013.01); *A61B 8/12* (2013.01); *A61B 8/40* (2013.01); *A61B 8/5238* (2013.01); *A61B 34/20* (2016.02); *A61B 5/015* (2013.01); *A61B 5/0456* (2013.01); *A61B 5/066* (2013.01); *A61B 5/7425* (2013.01); *A61B 6/4441* (2013.01); *A61B 34/10* (2016.02); *A61B 2017/00243* (2013.01); *A61B 2017/00703* (2013.01); *A61B 2034/2051* (2016.02); *A61B 2034/2072* (2016.02); *A61B 2090/364* (2016.02); *A61B 2090/365* (2016.02); *A61B 2090/376* (2016.02); *A61B 2090/3958* (2016.02)

(56) References Cited

U.S. PATENT DOCUMENTS

| | | |
|---|---|---|
| 3,990,296 A | 11/1976 | Erikson |
| 4,398,540 A | 8/1983 | Takemura et al. |
| 4,737,794 A | 4/1988 | Jones |
| 5,016,642 A | 5/1991 | Dukes et al. |
| 5,152,290 A | 10/1992 | Freeland |
| 5,159,931 A | 11/1992 | Pini |
| 5,318,025 A | 6/1994 | DuMoulin et al. |
| 5,360,008 A | 11/1994 | Campbell |
| 5,398,691 A | 3/1995 | Martin |
| 5,445,150 A | 8/1995 | Dumoulin et al. |
| 5,453,686 A | 9/1995 | Anderson |
| 5,529,070 A | 6/1996 | Augustine et al. |
| 5,540,928 A | 7/1996 | Edelman et al. |
| 5,577,502 A | 11/1996 | Darrow et al. |
| 5,588,432 A | 12/1996 | Crowley et al. |
| 5,622,174 A | 4/1997 | Yamazaki |
| 5,638,819 A * | 6/1997 | Manwaring et al. ......... 600/424 |
| 5,646,525 A | 7/1997 | Gilboa |
| 5,669,385 A | 9/1997 | Pesque et al. |
| 5,690,113 A | 11/1997 | Sliwa et al. |
| 5,724,982 A | 3/1998 | Schnurer et al. |
| 5,730,129 A | 3/1998 | Darrow et al. |
| 5,740,808 A | 4/1998 | Panescu et al. |
| 5,744,953 A | 4/1998 | Hansen |
| 5,787,889 A | 8/1998 | Edward et al. |
| 5,797,849 A | 8/1998 | Vesely et al. |
| 5,806,521 A | 9/1998 | Morimoto et al. |
| 5,810,008 A | 9/1998 | Dekel et al. |
| 5,830,145 A | 11/1998 | Tenhoff |
| 5,830,222 A | 11/1998 | Makower |
| 5,846,200 A | 12/1998 | Schwartz |
| 5,899,860 A | 5/1999 | Pfeiffer et al. |
| 5,906,578 A | 5/1999 | Rajan et al. |
| 5,913,820 A | 6/1999 | Bladen et al. |
| 5,924,989 A | 7/1999 | Polz |
| 5,928,248 A | 7/1999 | Acker |
| 5,935,075 A | 8/1999 | Casscells et al. |
| 5,938,606 A | 8/1999 | Bonnefous |
| 5,949,491 A | 9/1999 | Callahan et al. |
| 5,955,879 A | 9/1999 | Durdle et al. |
| 5,957,844 A | 9/1999 | Dekel et al. |
| 5,967,980 A | 10/1999 | Ferre et al. |
| 5,976,088 A | 11/1999 | Urbano et al. |
| 5,993,390 A | 11/1999 | Savord et al. |
| 5,994,690 A | 11/1999 | Kulkarni et al. |
| 6,006,126 A | 12/1999 | Cosman |
| 6,016,439 A * | 1/2000 | Acker ........................ 600/411 |
| 6,030,343 A | 2/2000 | Chechersky et al. |
| 6,035,856 A | 3/2000 | LaFontaine et al. |
| 6,047,080 A | 4/2000 | Chen et al. |
| 6,134,003 A | 10/2000 | Tearney et al. |
| 6,148,095 A | 11/2000 | Prause et al. |
| 6,167,296 A * | 12/2000 | Shahidi ........................ 600/427 |
| 6,169,917 B1 | 1/2001 | Masotti et al. |
| 6,175,669 B1 | 1/2001 | Colston et al. |
| 6,195,450 B1 | 2/2001 | Qian et al. |
| 6,213,945 B1 | 4/2001 | Tynan et al. |
| 6,216,029 B1 | 4/2001 | Paltieli |
| 6,228,028 B1 | 5/2001 | Klein et al. |
| 6,233,476 B1 | 5/2001 | Strommer et al. |
| 6,246,898 B1 | 6/2001 | Vesely et al. |
| 6,275,724 B1 | 8/2001 | Dickinson et al. |
| 6,317,621 B1 | 11/2001 | Graumann et al. |
| 6,321,109 B2 | 11/2001 | Ben-Haim et al. |
| 6,344,863 B1 | 2/2002 | Capelli et al. |
| 6,368,285 B1 * | 4/2002 | Osadchy ............ A61B 5/0064 382/131 |
| 6,381,350 B1 | 4/2002 | Klingensmith et al. |
| 6,385,476 B1 | 5/2002 | Osadchy et al. |
| 6,390,982 B1 | 5/2002 | Bova et al. |
| 6,405,072 B1 | 6/2002 | Cosman et al. |
| 6,416,476 B1 | 7/2002 | Ogasawara et al. |
| 6,432,041 B1 | 8/2002 | Taniguchi et al. |
| 6,470,207 B1 | 10/2002 | Simon et al. |
| 6,498,944 B1 | 12/2002 | Ben-Haim et al. |
| 6,501,981 B1 | 12/2002 | Schweikard et al. |
| 6,546,271 B1 | 4/2003 | Reisfeld |
| 6,556,695 B1 | 4/2003 | Packer et al. |
| 6,589,163 B2 | 7/2003 | Aizawa et al. |
| 6,626,902 B1 | 9/2003 | Kucharczyk et al. |
| 6,671,538 B1 * | 12/2003 | Ehnholm et al. ............. 600/425 |
| 6,730,030 B2 | 5/2004 | Palti |
| 6,733,458 B1 | 5/2004 | Steins et al. |
| 6,773,393 B1 | 8/2004 | Taniguchi et al. |
| 6,775,404 B1 | 8/2004 | Pagoulatos et al. |
| 6,788,967 B2 | 9/2004 | Ben-Haim et al. |
| 6,895,267 B2 | 5/2005 | Panescu et al. |
| 6,917,827 B2 * | 7/2005 | Kienzle, III .................. 600/427 |
| 7,007,699 B2 | 3/2006 | Martinelli et al. |
| 7,159,592 B1 | 1/2007 | Makower et al. |
| 7,195,587 B2 | 3/2007 | Taniguchi et al. |
| 7,197,354 B2 | 3/2007 | Sobe |
| 7,235,084 B2 | 6/2007 | Skakoon et al. |
| 7,263,397 B2 | 8/2007 | Hauck et al. |
| 7,343,195 B2 | 3/2008 | Strommer et al. |
| 7,386,339 B2 | 6/2008 | Strommer et al. |
| 7,398,116 B2 | 7/2008 | Edwards |
| 7,527,597 B2 | 5/2009 | Sandlen et al. |
| 7,739,090 B2 | 6/2010 | Charbel et al. |
| 7,778,688 B2 | 8/2010 | Strommer |
| 7,881,769 B2 | 2/2011 | Sobe |
| 8,126,534 B2 | 2/2012 | Maschke |
| 8,332,013 B2 | 12/2012 | Strommer |
| 8,442,618 B2 | 5/2013 | Strommer et al. |
| 2001/0031919 A1 | 10/2001 | Strommer et al. |
| 2001/0044578 A1 | 11/2001 | Ben-Haim et al. |

(56) References Cited

U.S. PATENT DOCUMENTS

| | | |
|---|---|---|
| 2002/0007124 A1 | 1/2002 | Woodward |
| 2002/0049375 A1 | 4/2002 | Strommer et al. |
| 2002/0193686 A1 | 12/2002 | Gilboa |
| 2003/0074011 A1 | 4/2003 | Gilboa et al. |
| 2004/0034297 A1 | 2/2004 | Darrow et al. |
| 2004/0097804 A1 | 5/2004 | Sobe |
| 2004/0116775 A1 | 6/2004 | Taniguchi et al. |
| 2004/0138548 A1 | 7/2004 | Strommer et al. |
| 2004/0215071 A1 | 10/2004 | Frank et al. |
| 2005/0033149 A1 | 2/2005 | Strommer et al. |
| 2005/0049493 A1 | 3/2005 | Kerby et al. |
| 2005/0107688 A1 | 5/2005 | Strommer et al. |
| 2005/0129176 A1 | 6/2005 | Kokubun et al. |
| 2005/0197557 A1 | 9/2005 | Strommer et al. |
| 2005/0197566 A1 | 9/2005 | Strommer et al. |
| 2006/0058647 A1 | 3/2006 | Strommer et al. |
| 2006/0064006 A1 | 3/2006 | Strommer et al. |
| 2006/0079745 A1 | 4/2006 | Viswanathan |
| 2006/0089706 A1 | 4/2006 | Plaia et al. |
| 2007/0287901 A1 | 12/2007 | Strommer et al. |
| 2008/0175463 A1 | 7/2008 | Strommer et al. |
| 2008/0221440 A1 | 9/2008 | Iddan et al. |
| 2008/0221442 A1 | 9/2008 | Tolkowsky et al. |
| 2009/0182224 A1 | 7/2009 | Shmarak et al. |
| 2010/0331950 A1 | 12/2010 | Strommer |
| 2011/0230758 A1 | 9/2011 | Eichler |

FOREIGN PATENT DOCUMENTS

| | | |
|---|---|---|
| JP | 62032304 | 2/1987 |
| JP | 8500441 | 1/1996 |
| JP | 11110114 | 4/1999 |
| JP | 2001170027 | 6/2001 |
| JP | 2002200058 | 7/2002 |
| JP | 2004533863 | 11/2004 |
| JP | 2007502187 | 2/2007 |
| WO | WO-96/05768 | 2/1996 |
| WO | WO-96/41119 | 12/1996 |
| WO | WO-97/29682 | 8/1997 |
| WO | WO-97/29685 | 8/1997 |
| WO | WO 97/29685 * | 8/1997 |
| WO | WO-97/036143 | 10/1997 |
| WO | WO-99/43253 | 9/1999 |
| WO | WO-00/10456 | 3/2000 |
| WO | WO-00/16684 | 3/2000 |
| WO | WO-02/064011 | 8/2002 |
| WO | WO-03/059167 | 7/2003 |
| WO | WO-2004/060157 | 7/2004 |
| WO | WO-2004/062501 | 7/2004 |
| WO | WO-2005/039391 | 5/2005 |

OTHER PUBLICATIONS

Author: Panza, Julio A Title: Real-time three-dimensional echocardiography: An overview Citation: The International Journal of Cardiovascular Imaging 17:227-235, 2001.

* cited by examiner

METHOD AND SYSTEM FOR SUPERIMPOSING VIRTUAL ANATOMICAL LANDMARKS ON AN IMAGE

CROSS-REFERENCE TO RELATED APPLICATIONS

This application is a continuation-in-part (CIP) of U.S. application Ser. No. 11/233,420 filed Sep. 16, 2005 (the '420 application), now U.S. Pat. No. 8,442,618, which is a continuation-in-part (CIP) of U.S. application Ser. No. 10/986,567 filed Nov. 10, 2004 (the '567 application), now U.S. Pat. No. 9,572,519, which is a continuation-in-part (CIP) of U.S. application Ser. No. 10/938,395 filed on Sep. 9, 2004 (the '395 application), now U.S. Pat. No. 7,778,688. The '420 application, the '567 application, and the '395 application are hereby incorporated by reference as though fully set forth herein. As to U.S. application Ser. No. 09/949,160, filed on Sep. 7, 2001 (the '160 application), now U.S. Pat. No. 7,343,195, U.S. application Ser. No. 09/782,528, filed on Feb. 13, 2001 (the '528 application), now U.S. Pat. No. 7,386,339, and U.S. application Ser. No. 09/314,474, filed on May 18, 1999 (the '474 application), now U.S. Pat. No. 6,233,476, the '160 application, the '528 application, and the '474 application are hereby incorporated by reference as though fully set forth herein.

BACKGROUND OF THE INVENTION a. Field of the Invention

The instant invention relates generally to medical imaging and navigation systems and more particularly to a method and system for superimposing virtual anatomical landmarks on an image.

b. Background Art

In the field of medical imaging and navigation, anatomical landmarks within a region of interest (i.e., in a patient's body) are often poorly visible or even invisible on a fluoroscopic image of the region of interest. This lack of visibility may limit or even prevent identification of such anatomical landmarks by a physician during a medical procedure.

There is therefore a need for an improved method and system for superimposing marks on an image.

BRIEF SUMMARY OF THE INVENTION

One advantage of the methods and apparatus described, depicted and claimed herein relates to the ability to accurately and more flexibly specify virtual landmarks within a region of interest in a patient's body (or cavity thereof) without the need to first traverse a path with the location-enabled medical tool in order to first compute a trajectory. Another advantage relates to the ability to designate virtual landmarks in a region of interest (including a cavity such as a heart chamber) and not just in a body lumen.

This disclosure is directed to an apparatus and method for superimposing a virtual landmark on an image of a region of interest in a patient's body. The apparatus includes a localization system and a control unit. The localization system is configured to produce location readings with respect to points within the region of interest in accordance with an output of a location sensor disposed in a medical device as the device moves within the region of interest. The location readings are associated with a reference coordinate system, which is registered with an image coordinate system associated with the image. The control unit provides a user interface configured to receive a signal (e.g., from a user) to record a location reading in accordance with the output of the location sensor, where the recorded location reading corresponds to a desired point within the region of interest where the virtual landmark is to be established. The signal, in one embodiment, may be an input provided by the user at the desired point on the image where the virtual landmark is to be established. The control unit is configured to determine a target location in the image coordinate system, corresponding to the recorded location reading. The control unit is further configured to superimpose a representation of the virtual landmark on the image at the target location.

In an further embodiment, the control unit is further configured to (1) modify the recorded location reading to compensate for motion at the desired point in the region of interest between a first time when the image was acquired and a second time when the location reading was recorded; and (2) transform the motion-compensated location reading from the reference coordinate system to the image coordinate system. The motion compensation may be performed in accordance with various motion inputs indicative of the motion of the region of interest. The motion inputs may include an input from a patient reference sensor (PRS) configured to be affixed to the patient and providing PRS location readings indicative of patient body movements and respiration-induced movements, an input from an ECG monitor indicative of heartbeat-induced movements and an input from an internal location reference sensor local to the region of interest.

A corresponding method is also presented.

These and other benefits, features, and capabilities are provided according to the structures, systems, and methods depicted, described and claimed herein.

DETAILED DESCRIPTION OF THE INVENTION

Figure 1:
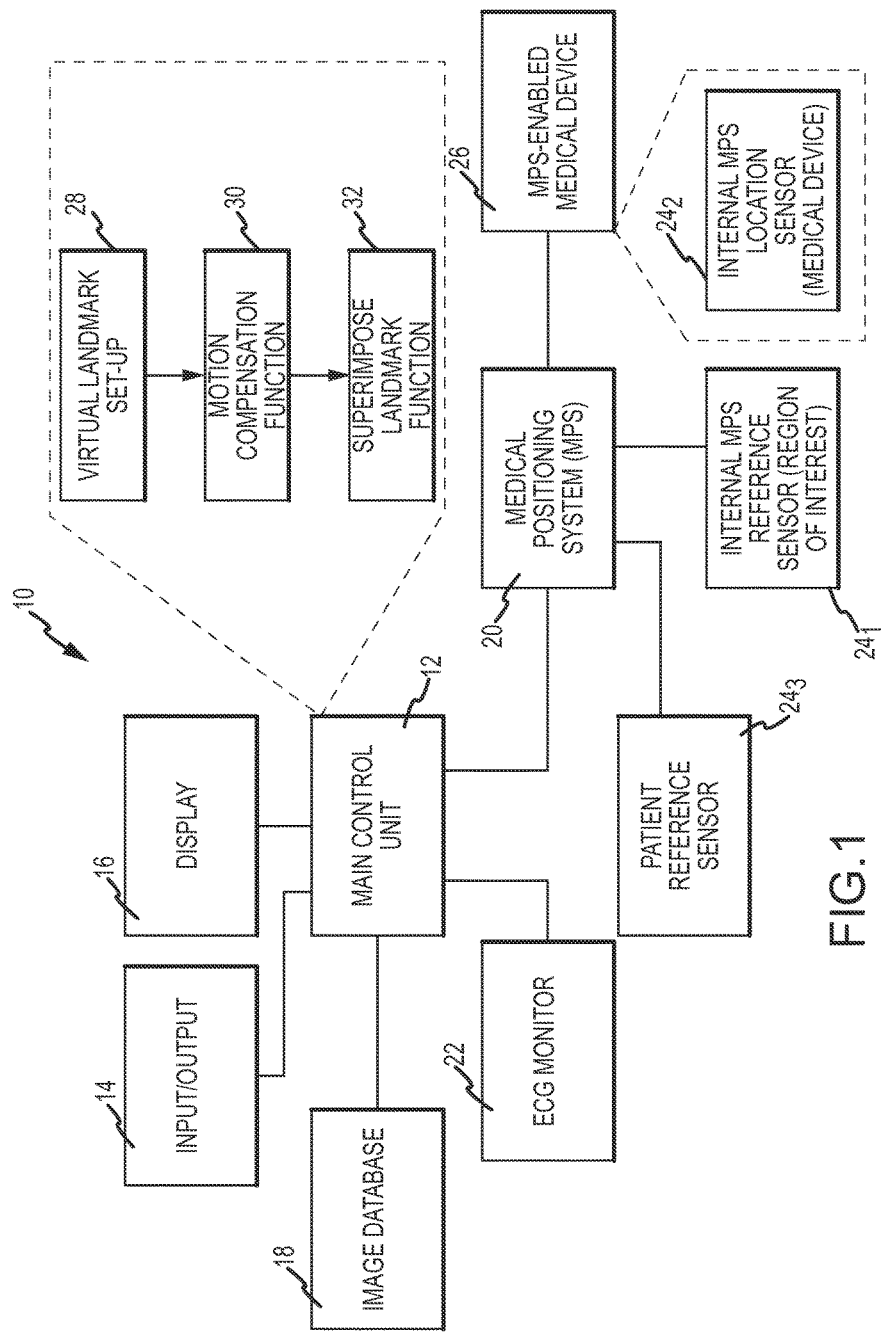
FIG. 1 is a schematic and block diagram view of a system incorporating an embodiment for superimposing virtual anatomical landmarks on an image.

Referring now to the drawings wherein like reference numerals are used to identify identical components in the various views, FIG. 1 is a diagrammatic view of a system 10 in which aspects of an apparatus and method for superimposing virtual anatomical landmarks on an image may be embodied. It should be understood that while embodiments will be described in connection with a magnetic field-based positioning system in a catheter-lab environment, this is exemplary only and not limiting in nature.

As described in the Background, anatomical landmarks within a region of interest in a patient's body are often only poorly visible or even invisible on a fluoroscopic image of the region. This lack of visibility may encumber the identification of the landmark by a physician during a medical procedure. There is therefore a desire to improve the visibility of an anatomical landmark, whether on live fluoroscopic images or still or cine-loops captured at an earlier time. Embodiments of the invention establish a virtual anatomical landmark on an image, which is configured to be readily visible, in the same location in the region of interest where the anatomical landmark exists, thus aiding navigation during a medical procedure.

With continued reference to FIG. 1, the system 10 as depicted includes a main control unit 12 (e.g., a processor) having various input/output mechanisms 14, a display 16, an image database 18, a localization system such as a medical positioning system (MPS) 20, an electrocardiogram (ECG) monitor 22, one or more MPS location sensors respectively designated $24_1$, $24_2$ and $24_3$, and an MPS-enabled medical device or tool 26 which itself includes an MPS location sensor (i.e., sensor $24_2$).

The control unit 12, in a computer-implemented embodiment, is programmed to perform a plurality of functions, including the functions of (1) establishing a virtual anatomical landmark, as performed by block 28 (i.e., associating a virtual anatomical landmark with a corresponding anatomical location); (2) compensating for motions in the regions of interest with respect to the location of the virtual landmark, as performed by block 30; and (3) superimposing a representation of the virtual anatomical landmark on an image, as performed by block 32.

The virtual anatomical landmark set-up block 28 is configured generally to present a user interface configured to allow a user (i.e., a physician) to designate when the MPS-enabled medical tool 26 has been maneuvered to a desired point in the region of interest where the virtual landmark is to be established. The block 28 is further configured to record the device MPS location reading when so indicated by the user.

The motion compensation block 30 is configured generally to modify the recorded MPS location reading so as to account for patient body, respiration and cardiac related motions between the time when the recorded location reading (for the virtual landmark) was acquired and some earlier time (e.g., the time when the image on which the virtual landmark is to be superimposed). The motion compensation block 30 will take as inputs a number of signals indicative of the motion in the region of interest, as described below. The motion-compensated location reading (in the reference coordinate system) is then transformed into a corresponding target location in the image coordinate system. The image coordinate system is preferably registered with the reference coordinate system.

The superimposing function block 32 is configured generally to superimpose a representation of the virtual landmark on the image of the region of interest, which may have been acquired at an earlier time, may be an image in a cine-loop acquired at an earlier time or may be "live" fluoroscopy. The virtual landmark is superimposed at the target location in the image coordinate system, which corresponds to the actual anatomical landmark designated by the user. The resulting composite image may then be displayed to the user (e.g., a physician) on the display 16. The user may use the composite image for navigation purposes during a medical procedure. Superimposing function block 32 may include conventional apparatus and methods for performing the superimposing function (e.g., may include a superimposing processor).

The system 10 enables placement of virtual anatomical landmarks in a recorded location of the MPS-enabled medical device 26 rather than as pointers along a path (i.e., computed trajectory) that the device has traversed, as described in the Background. Embodiments of the invention provide greater flexibility in at least two different ways: (1) from a procedural point of view, a virtual anatomical landmark can be recorded without requiring the user (or system) to record medical device positions throughout a traveled path; and (2) the anatomy serviceable by embodiments of the invention is not limited to tubular organs like arteries (i.e., body lumens) and includes open cavities such as a heart chamber.

The input/output mechanisms 14 may comprise conventional apparatus for interfacing with a computer-based control unit, for example, a keyboard, a mouse, a tablet, a foot pedal, a switch or the like. The display 16 may also comprise conventional apparatus.

Embodiments consistent with the invention may find use in navigation applications that use imaging of a region of interest (as described above). Therefore the system 10 may include the image database 18. The image database 18 may be configured to store image information relating to the patient's body, for example a region of interest surrounding a destination site for the medical tool and/or multiple regions of interest along a navigation path contemplated to be traversed by the medical tool to reach the destination site. The image data in the database 18 may comprise known image types including (1) one or more two-dimensional still images acquired at respective, individual times in the past; (2) a plurality of related two-dimensional images obtained in real-time from an image acquisition device (e.g., fluoroscopic images from an x-ray imaging apparatus, such as that shown in exemplary fashion in FIG. 2) wherein the image database acts as a buffer ("live" fluoroscopy); and/or (3) a sequence of related two-dimensional images defining a cine-loop (CL) wherein each image in the sequence has at least an ECG timing parameter associated therewith adequate to allow playback of the sequence in accordance with acquired real-time ECG signals obtained from the ECG monitor 22. It should be understood that the foregoing are examples only and not limiting in nature. For example, the image database may also include three-dimensional image data as well. It should be further understood that the images may be acquired through any imaging modality now known or hereafter developed for example X-ray, ultra-sound, computerized tomography, nuclear magnetic resonance or the like.

The MPS 20 is configured to serve as the localization system and therefore to determine positioning (localization) data with respect to one or more of the MPS location sensors $24_i$ (where i=1 to n) and output a respective location reading. The location readings may each include at least one or both of a position and an orientation (P&O) relative to a reference coordinate system, which may be the coordinate system of the MPS 20. The P&O may be expressed as a position (i.e., a coordinate in three axes X, Y and Z) and orientation (i.e., an azimuth and elevation) of the magnetic field sensor in the magnetic field relative to a magnetic field generator(s) or transmitter(s). Other expressions of a P&O (e.g., other coordinates systems) are known in the art and fall within the spirit and scope of the present invention (e.g., see for example FIG. 3 and associated text of U.S. Pat. No. 7,343, 195 entitled "METHOD AND APPARATUS FOR REAL TIME QUANTITATIVE THREE-DIMENSIONAL IMAGE RECONSTRUCTION OF A MOVING ORGAN AND INTRA-BODY NAVIGATION" to Strommer et al, incorporated by reference in its entirety, viz. location [X, Y, Z] and orientation (angles $\alpha$, $\beta$, and $\chi$)).

Figure 2:
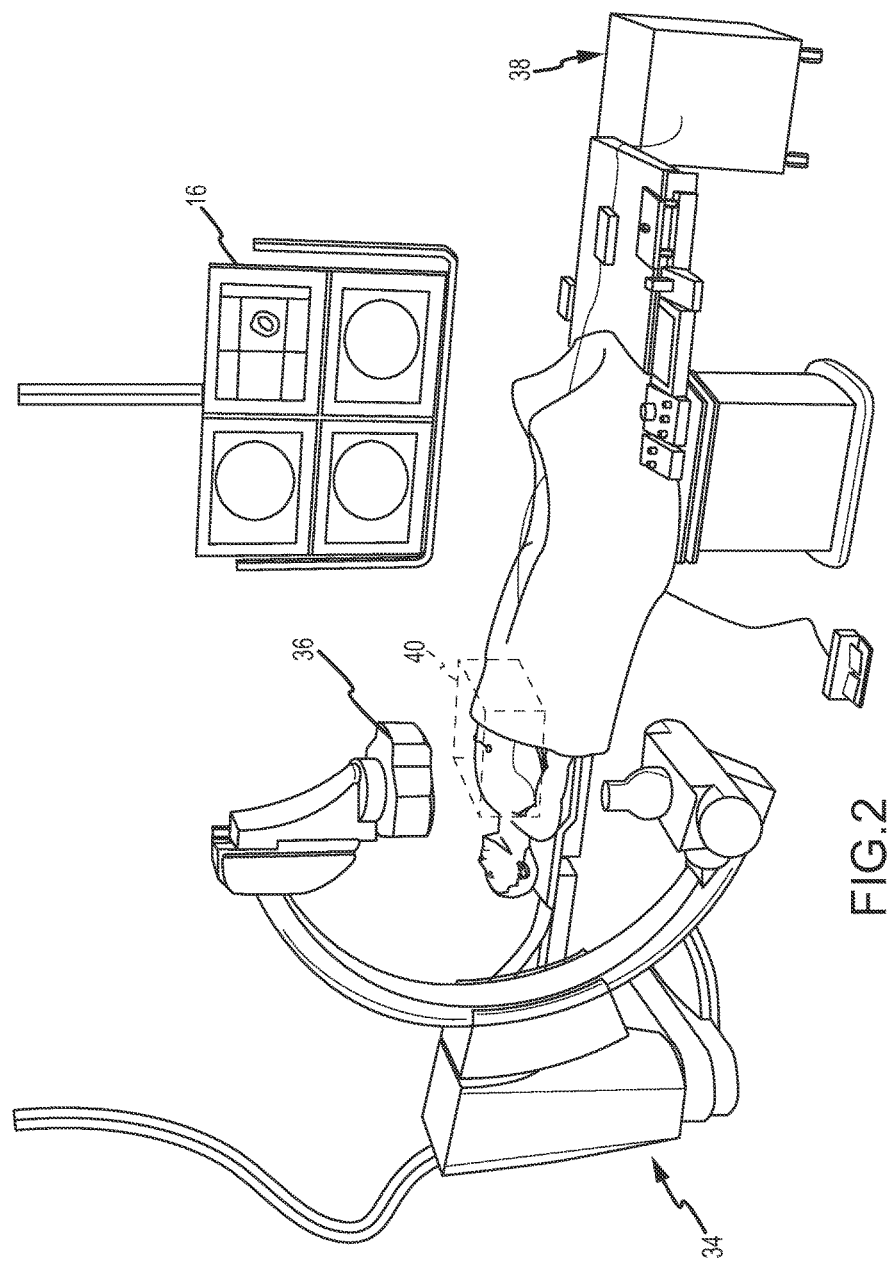
FIG. 2 is a diagrammatic view of the system of FIG. 1 in a catheter-lab environment.

The MPS 20 determines respective locations (i.e., P&O's) in the reference coordinate system based on capturing and processing signals received from the magnetic field sensors $24_i$ while such sensors are disposed in a controlled low-strength AC magnetic field (see FIG. 2). Each sensor may comprise one or more magnetic field detection coil(s), and it should be understood that variations as to the number of coils, their geometries, spatial relationships, the existence or absence of cores and the like are possible. From an electromagnetic perspective, these sensors develop a voltage that is induced on the coil residing in a changing magnetic field, as contemplated here. The sensors $24_i$ are thus configured to detect one or more characteristics of the magnetic field(s) in which they are disposed and generate an indicative signal, which is further processed by the MPS 20 to obtain a respective P&O thereof. For one example of a sensor, see U.S. Pat. No. 7,197,354 entitled SYSTEM FOR DETERMINING THE POSITION AND ORIENTATION OF A CATHETER issued to Sobe, hereby incorporated by reference in its entirety.

FIG. 1 shows a first MPS location reference sensor $24_1$ for purposes of providing a motion compensation input indicative of motion local to the region of interest, for example as seen by reference to co-pending U.S. patent application Ser. No. 12/650,932, filed Dec. 31, 2009, entitled "COMPENSATION OF MOTION IN A MOVING ORGAN USING AN INTERNAL POSITION REFERENCE SENSOR", owned by the common assignee of the present invention and hereby incorporated by reference in its entirety herein. One or more of such location reference sensors $24_1$ may be realized using, for example, disposable invasive medical tools and/or devices that may be used in the procedure even apart from their function as "carriers" of location reference sensors. Other sensor types may be used for motion compensation, including without limitation accelerometers as well as others known in the art.

The second MPS location sensor $24_2$ is associated with the MPS-enabled medical tool 26, and may be, for example, disposed in the tip of a catheter as described below. The third MPS sensor—the patient reference sensor (PRS) $24_3$—is configured to provide a stable, positional reference of the patient's body so as to allow motion compensation for gross patient body movements and/or respiration-induced movements. In this regard, the PRS $24_3$ may be attached to the patient's manubrium sternum, a stable place on the chest, or other location that is relatively positionally stable. Furthermore, the PRS $24_3$ may be implemented by a multiplicity of physical sensors that are attached to different locations on the patient's body. Like the other MPS location sensors, the PRS $24_3$ is also configured detect one or more characteristics of the magnetic field in which it is disposed wherein the MPS 20, based on the sensor's output, provides a location reading (e.g., a position and orientation (P&O) reading) indicative of the PRS's three-dimensional position and orientation in the reference coordinate system.

An electro-cardiogram (ECG) monitor 22 can continuously detect an electrical timing signal of the heart organ through the use of a plurality of ECG electrodes (not shown), which may be externally-affixed to the outside of a patient's body. The timing signal generally corresponds to and is indicative of the particular phase of the cardiac cycle, among other things. Generally, the ECG signal(s) may be used by the control unit 12 (e.g., sampled to provide a real time value) for ECG synchronized play-back of a previously captured sequences of images (cine loop) stored in the database 18. In certain embodiments, the ECG signal may also be used for motion compensation. The ECG monitor 22 and ECG-electrodes may both comprise conventional components.

FIG. 2 is a diagrammatic view of the system 10 as incorporated into a larger system that has self-contained imaging capability. It should be understood that while the approach for superimposition of virtual anatomical landmarks on an image, as described herein in certain embodiments does not require extensive use of fluoroscopy, other aspects of any medical procedure may involve such use, at least intermittently. The system 10 is shown as being incorporated into a fluoroscopic imaging system 34, which may include commercially available fluoroscopic imaging components (i.e., "Catheter Lab"). The MPS 20, in a magnetic field-based embodiment, includes a magnetic transmitter assembly (MTA) 36 and a magnetic processing core 38 for determining location (position and orientation (P&O)) readings. The MTA 36 is configured to generate the magnetic field(s) in and around the patient's chest cavity, in a pre-defined three-dimensional space identified as a motion box 40. The MPS sensors $24_i$ (where i=1, 2, . . . , n) as described above are configured to sense one or more characteristics of the magnetic field(s) and when the sensors are in the motion box 40, each generate a respective signal that is provided to the magnetic processing core 38. The processing core 38 is responsive to these detected signals and is configured to calculate respective three-dimensional position and orientation (P&O) readings for each MPS sensor $24_i$ in the motion box 40. Thus, the MPS system 20 enables real-time tracking of each sensor $24_i$ in three-dimensional space.

The positional relationship between the image coordinate system and the MPS coordinate system (e.g., the reference coordinate system) may be calculated based on a known optical-magnetic calibration of the system (e.g., established during setup), since the positioning system and imaging system may be considered fixed relative to each other in such an embodiment. However, for other embodiments using other imaging modalities, including embodiments where the image data is acquired at an earlier time and then imported from an external source (e.g., imaging data stored in database 18), a registration step registering the MPS coordinate system and the image coordinate system may need to be performed so that MPS location readings can be properly transformed into the image coordinate system of any particular image being used. Once registered, a coordinate (i.e., position and orientation values) in one coordinate system may be transformed into a corresponding coordinate in the other coordinate system through the transformations established during the registration process, a process known generally in the art, for example as seen by reference to U.S. Patent Application Publication US 2006/0058647 referred to above in the Background. One exemplary embodiment of an MPS 20 will be described in greater detail below in connection with FIG. 7.

Figure 3:
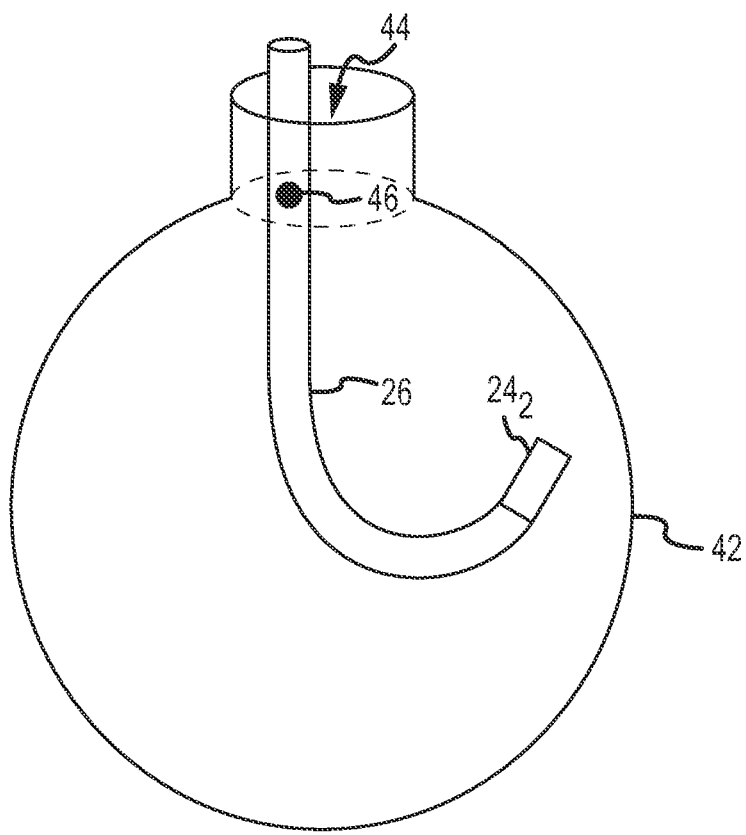
FIG. 3 is a diagrammatic view of a medical tool equipped with an MPS location sensor used to designate a desired point in a region of interest for a virtual anatomical landmark.

FIG. 3 is a diagrammatic view of a medical tool being inserted in a region of interest in a patient's body. The disclosed method and apparatus overcomes the disadvantages of the prior art by providing the capability of superimposing a virtual anatomical landmark on an image based on the recorded location of a MPS enabled medical tool, as explained more fully below.

In the illustrative embodiment of FIG. 3, the medical tool takes the form of a catheter 26 having an MPS location sensor $24_2$ at a distal end. The catheter 26 may be maneuvered by a physician towards a desired region of interest 42 (e.g., the right atrium of the heart) contained within the patient's body, which maneuvering involves passing the catheter 26 through an insertion region 44 (i.e., in this example where the destination site is the right atrium, the Superior Vena Cava (SVC) is the insertion region). In this example, the SVC 44 constitutes the anatomical landmark. When the catheter tip is positioned near the anatomical landmark (SVC 44), the location 46 of the catheter tip, as determined in accordance with the output of the MPS sensor $24_1$, and thus also the location of the anatomical landmark, is recorded.

In one embodiment, the control unit 12 is configured to determine the location 46 through interaction with the user. Specifically, the user may visually detect when the catheter 26 passes near the anatomical landmark—the SVC 44, generally according to an inspection of a live or pre-recorded x-ray image of the region of interest 42, and more particularly when a desired part of the catheter (e.g., the tip) passes through the SVC 44. When the user believes that the catheter is at the desired landmark, he or she marks it through interaction with a user interface (more below) provided by the control unit 12. To supplement recognition, the control unit 12, in an embodiment, may be optionally configured superimpose a representation of the catheter's tip location on the x-ray image being displayed to the user, for example, in the form of cross-hairs or the like.

As described above, the control unit 12 includes a user interface (e.g., a graphical user interface (GUI)) configured to receive the user's "mark" as an input signal constituting the request to record the MPS location reading. The signal may take the form of some user-initiated action such as actuation of a joystick, a push button, a pointing device (e.g., mouse, stylus and digital tablet, track-ball, touch pad) or by any other conventional means. The user interface of the control unit 12 recognizes the user request and the control unit 12 then records the MPS location reading corresponding to the location 46. To facilitate marking the desired point in the region of interest, the control unit 12 may be configured to perform the following general steps: (i) presenting the image of the region of interest on the display; (ii) receiving from the user a graphical designation on the image defining the location of the mark; and (iii) determining the location of the mark in the reference coordinate system of the MPS in accordance with the user-specified graphical designation, which involves recording the MPS location reading of the medical device.

As described above, the coordinate system of the x-ray image (the image coordinate system) is registered with the reference coordinate system of the MPS 20. Therefore, the location of the anatomical landmark in the image coordinate system may be determined through application of the one or more transformation matrices already defined relating the respective coordinate systems. Through the foregoing, a virtual landmark is associated with an anatomical location (desired point) in the region of interest.

It should be appreciated that MPS 20 provides location (i.e., P&O) readings in a reference coordinate system as the MPS-enabled tool moves within the motion box 40. However, during a medical procedure, the patient may also move. To properly interpret an MPS location reading in the context of the patient's body, the patient's motion must also be taken into account by the system 10. Motion compensation is needed, generally, to properly locate the tool within the patient's body, as known, and more specifically, in accordance with the invention, to properly locate a virtual anatomical landmark on an image. Moreover, as new images are displayed by the system 10, the control unit 12 uses motion compensation to ensure that the virtual landmark is accurately located on those images as well, since such images may have been acquired at different times subject to different motion influences on the region of interest (e.g., patient's body movements, respiration-induced movements, cardiac (heartbeat) movements, etc.). Accordingly, in an embodiment, motion compensation is performed, for example, by the motion compensation block 30.

In this regard, the control unit 12 is configured to continuously record signals indicative of the motion in the region of interest, which includes the anatomical landmark (e.g., SVC 44). These motion inputs may include the cardiac phase (i.e., via the ECG signal indicative of heart motion), location readings of the PRS $24_3$ (i.e., indicative of patient gross (body) and respiration-induced motion) as well as (optionally) location readings from the internal MPS reference sensor $24_1$, (i.e., indicative of internal movements measured locally at or within the region of interest, thus having a high correlation with the movement of the anatomical landmark). Variations and combinations of the foregoing are possible, for example only, including the use of multiple PRS's, the use of a PRS in a location other than on the patient chest, and/or the use of other respiratory indicators (e.g., patch impedance data available in the commercially available systems such as the St. Jude Medical EnSite™ Navx electrophysiology mapping and navigation system, as more particularly seen by reference to U.S. Pat. No. 7,263,397 issued to Hauck et al. entitled METHOD AND APPARATUS FOR CATHETER NAVIGATION AND LOCATION AND MAPPING IN THE HEART, assigned to the common assignee of the present invention, and hereby incorporated by reference in its entirety).

The motion compensation block 30 modifies the recorded MPS location reading for the motion of the region of interest between the time when the recorded MPS location reading was obtained and an earlier time (e.g., an earlier time when the image on which the user marked the anatomical landmark was acquired, and which may have been subjected to different motion influences). The motion compensation block 30 analyzes the various motion inputs and modifies the recorded MPS location reading accordingly. The motion compensation function block 30 may be performed in the main control unit 12 or in the MPS 20. A motion-compensated location (P&O) reading of the virtual anatomical landmark in the MPS reference coordinate system can be transformed into a corresponding coordinate in the image coordinate system.

In this regard, for a still image, typically, once the virtual landmark P&O has been transformed into the image coordinate system, the representation of the landmark that is superimposed on the still image will not move. However, this is true only for the case where the motion compensation function is evaluated once when the landmark P&O is transformed and is not thereafter adjusted. Note that in an embodiment where the motion compensation function is computed and performed substantially continuously throughout a procedure, there may be cases where the compensation function at the time of the landmark assignment is different (e.g., less accurate) than the compensation function computed at a later time. In these cases, the system may superimpose the landmark at a slightly different location on the still image wherein the user may see a slight movement of the landmark. The updated location on the image better represents the landmark's P&O than the original location. Later in time, when a different image is to be displayed (e.g., such as in a cine-loop or an updated image in "live" fluoroscopy), the P&O of the virtual landmark in the image coordinate system will have to be motion compensated again (and transformed) before superimposing the virtual landmark on the different image. The P&Os of the virtual landmarks (like sensors' P&Os) are 3-dimensional. They are acquired over a certain range of cardiac motion and a certain range of respiratory motion. The motion compensation block, using the acquired P&Os of the landmark, together with their corresponding cardiac and respiratory states, converts these P&Os, in an embodiment, to a "canonical" cardiac and respiratory state. In an embodiment, the system 10 is configured to allow a user to adjust the landmark (e.g., to correct the landmark, if needed or desired).

In a still further embodiment, the virtual landmark (i.e., its P&O) may be used in connection with (i.e., superimposed on) image data from a different imaging source. In such an embodiment, when a different imaging source is used, registration between the coordinate system of the different image source and the gMPS coordinate system has to take place. In some cases (such as rotational angiography) the co-registration may be automatic, while in other cases some user interaction may be needed. Co-registration is aimed at both finding a transformation between the two coordinate systems and defining the "canonical" state of the external data. In this sense, ideally, after co-registration, in such an embodiment, the imported imaging data will have a cardiac phase and a respiratory state assigned to it. From that point on, the motion compensation can be performed in a manner similar to that performed for any "internal" imaging data (albeit using the different transformation). Of course, the level of accuracy to be expected with co-registration of different modalities can vary.

It should be noted that the ECG signal obtained from the ECG monitor 22 may be used for both synchronization of cine-loop playback as well as for motion compensation. For example, during playback (i.e., display of) of a series of images defining a cine-loop, the real-time ECG is used to compute the current cardiac phase, which in turn is used to select a cine frame from the series of frames to best match the real-time cardiac phase. But this is not the end of the process due to the fact that the real-time cardiac phase is continuous while the cine-loop contains only so many cine frames per cardiac cycle. It follows that the selected background image will never precisely match the real-time cardiac phase, and thus there will likely be a residual error. This error can be compensated for by the cardiac compensation function between the current phase and the phase associated with the selected frame (i.e., the cardiac phase at the time the selected frame was captured). The difference between this situation (i.e., a cine-loop composed of a series of frames or still images) and a projection on a single still image is that for the latter case, phase differences between the current phase and the selected frame's phase are generally much larger.

Figure 4:
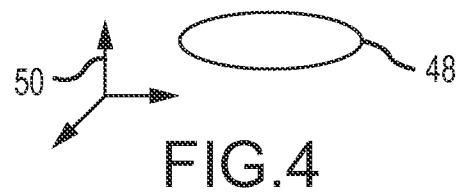
FIG. 4 is a diagrammatic view of a three-dimensional representation of a virtual anatomical landmark shown in relation to a reference coordinate system.

FIG. 4 is a diagrammatic illustration of a virtual anatomical landmark, generally referenced at 48 in accordance with another embodiment of the disclosed technique. The virtual landmark 48 may comprise a three-dimensional (3D) graphical construct defined in a 3D coordinate system 50 (e.g., the MPS coordinate system or another 3D coordinate system registered with the MPS coordinate system). In one embodiment, the size and shape of the virtual landmark 48 is predetermined in accordance with the nature of the anatomy. For example, the graphical construct of the inferior vena cava (IVC) will be a circular structure having an approximate diameter similar to a typical IVC diameter. In a further embodiment, the system 10 is configured to permit a user to scale (i.e., to adjust the size of) the predetermined object (e.g., a predetermined WC object) to accommodate variations in a patient in the size of the feature to be landmarked. In a further embodiment, the system 10 is configured to provide a user interface configured to allow the user to determine the shape of the virtual landmark. For example, the interface may be configured to present a drop down menu that allows the user to specify that the virtual landmark shape should be determined either on the basis of the current position of the MPS-enabled device or on a specific user-selected anatomical shape.

The display attributes of a virtual landmark, such as its color, may be set so as to be distinguishable from the background image. In an embodiment, the system 10 may set the color of a virtual landmark in accordance with the location of the landmark within the body (e.g., one color for virtual landmarks associated with pulmonary veins and a second, different color for fossa).

Figure 5A:
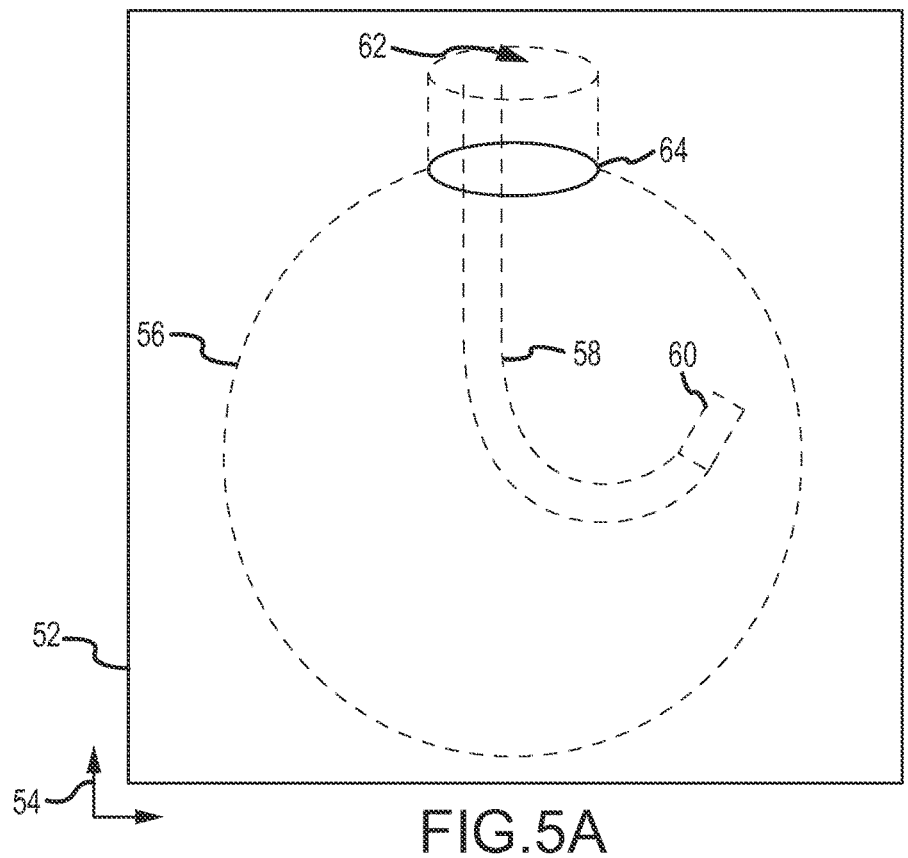
FIGS. 5A-5B are diagrammatic views of a virtual anatomical landmarks superimposed on two-dimensional images.

FIG. 5A is a diagrammatic illustration of a two-dimensional (2D) image, generally referenced at 52, in accordance with a still further embodiment of the disclosed technique. An image coordinate system 54 associated with the image 52 is registered with the reference coordinate system (e.g., the MPS coordinate system). The image 52 includes a representation of the region of interest 56, a representation of the catheter 58, a representation of the MPS location sensor 60, and a representation of the insertion region 62 through which the catheter passes to enter into the region of interest 56.

In the image 52, the representation of the region of interest 56 and in particular the insertion region 62 are poorly visible (indicated by dashed lines). Therefore, a virtual landmark 64 is superimposed on the image 52, using a graphical construct suitable for the landmark under consideration, at the location corresponding to the insertion region 62 (i.e., since the coordinate system of the virtual landmark is registered with the image coordinate system), thereby highlighting in the image 52 the insertion region 62, thereby improving the visibility of the insertion region to the user. Highlighting as used herein is intended to broadly include any display mechanism configured to enhance visibility to the user including without limitation different shapes, colors, light intensity levels, blinking and the like. In an embodiment, one mechanism involves overlaying a 3D graphic symbol over the image to represent the position and orientation of the virtual landmark. Different symbols, shapes and/or colors may be assigned to different virtual anatomical landmarks.

Figure 5B:
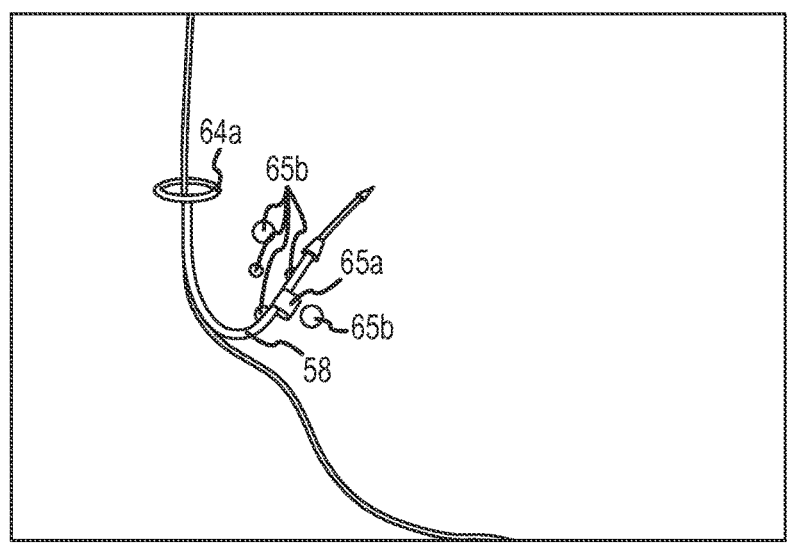

In some cases, the graphic representation corresponds to a feature of the anatomy. For example, as shown in FIG. 5B, an SVC landmark 64a may be a torus about the diameter of the actual SVC while for the CS ostium, a virtual landmark 65a may take the shape of a short cylinder about the diameter of a CS. Additional point landmarks 65b (represented by spheres) are shown that do not necessarily relate to any specific anatomical location, shape and/or size.

The location of the virtual anatomical landmark 64, is preferably compensated for errors originating from the motion of the region of interest (i.e., compensated of cardiac, respiratory and patient motions), as described above.

The superimposing function block 32 includes the capability of projecting the 3D representation of the virtual anatomical landmark on any one of (1) a previously recorded 2D image of the region of interest; (2) in the case of cine-loops (CL), onto each 2D image in the CL sequence; and/or (3) a live fluoroscopic image. The projection of the virtual landmark may in turn be graphically superimposed onto the image to be displayed on display 16 to form a composite image. The superimposing processor 32 may comprise components and approaches known in the art, for example, a processor configured to manipulate image data and data corresponding to the object to be superimposed, as seen by reference to U.S. Pat. Pub. 2006/0058647, application Ser. No. 11/233,420 entitled METHOD AND SYSTEM FOR DELIVERING A MEDICAL DEVICE TO A SELECTED POSITION WITHIN A LUMEN, to Strommer et al., hereby incorporated by reference in its entirety. As described, once the reference coordinate system and the image (e.g., x-ray imaging) coordinate system are co-registered, the motion-compensated 3D coordinates defining the virtual landmark's location may be multiplied by a coordinate transformation matrix to compute the corresponding 2D coordinates in the image coordinate system. This approach is exemplary only and not limiting in nature.

In addition, it should be understood that, although not shown, multiple virtual landmarks may be superimposed on an image representing respective anatomical landmarks, target regions and the like. In addition, when projecting the virtual anatomical landmarks on live fluoroscopic images, the resulting composite image may be aid the user in the navigation of tools that are not MPS-enabled (i.e., do not incorporate MPS location sensors).

Figure 6:
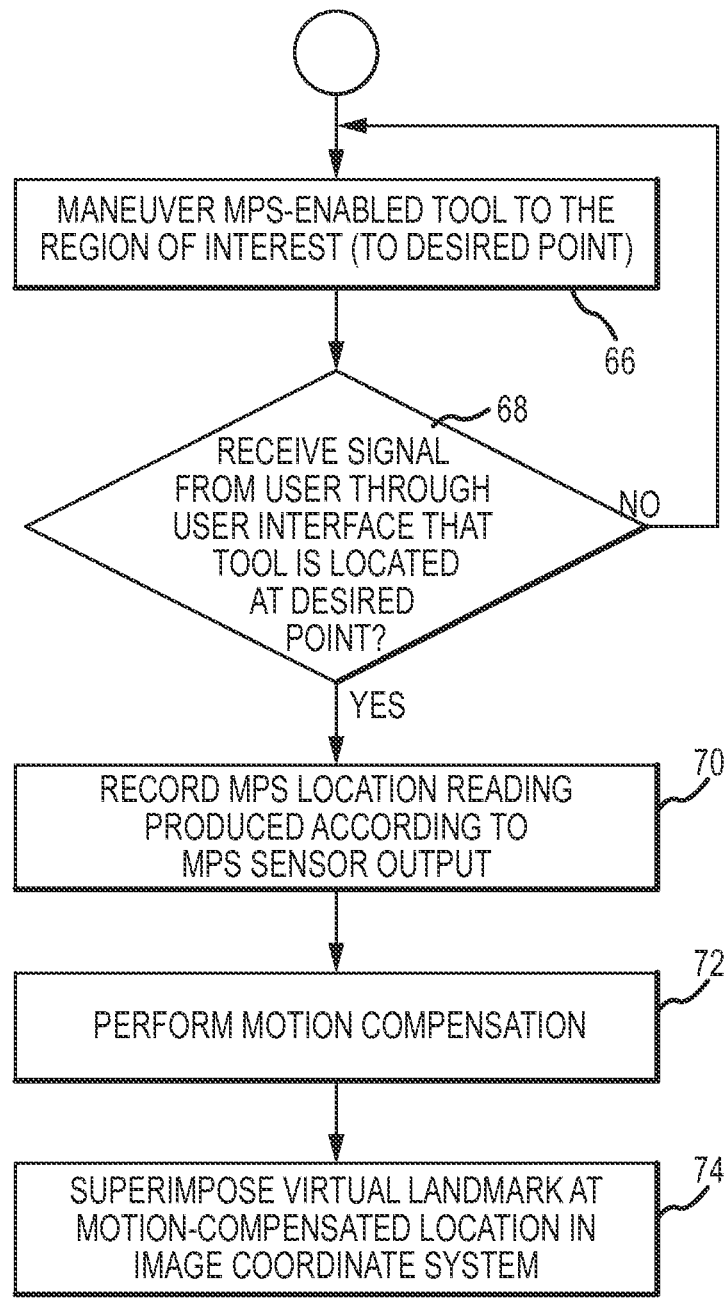
FIG. 6 is a flowchart showing a method for superimposing virtual anatomical landmarks on an image.

FIG. 6 is a flowchart of a method for superimposing a virtual anatomical landmark on an image. The method begins in step 66.

In step 66, the MPS-enabled medical tool is maneuvered to a desired point in a region of interest. During this step, the control unit 12 is constantly monitoring, through a user interface (e.g., a GUI), for receipt of an input signal from the user (e.g., a mouse-click, a mark by the user graphically designating on an image being displayed where the virtual landmark is to be established, etc.). The method proceeds to step 68.

In step 68, the control unit 12 checks whether the user has signaled to the control unit 12, via the user interface (UI), that he or she believes the MPS-enabled medical tool is near the location of the anatomical landmark or target region that is to receive a virtual landmark. If the answer is "NO" then the method branches back to step 66 where the user interface continues to monitor for an input signal while the physician may continue to maneuver the medical tool and/or assess the displayed image on display 16. However, if the answer in step 68 is "YES", then the method proceeds to step 70.

In step 70, the control unit 12 records an MPS location reading produced by the MPS 20 in accordance with the output of the MPS location sensor(s) in the medical tool. The recorded MPS location reading may take the form of a 3D coordinate (P&O) defined in the reference (MPS) coordinate system. The method proceeds to step 72.

In step 72, the recorded MPS location reading is motion compensated to remove errors originating due to motion of the region of interest between the time the recorded MPS location reading was obtained and an earlier time (e.g., when the image on which the mark was made was acquired). The control unit 12 then transforms the motion-compensated recorded location reading into a corresponding coordinate in the image coordinate system. This corresponding coordinate is the location of the anatomical landmark or region and defines the target location for the virtual anatomical landmark. The method proceeds to step 74.

In step 74, the control unit 12 determines a graphical representation of the virtual anatomical landmark, using a suitable graphical construct for the subject landmark, which may include a definition of its size and shape. The control unit 12 then superimposes the determined graphical representation onto the image at the target location in the image coordinate system. In the case where the graphical construct is a 3D graphical construct and the image is a 2D image, the control unit 12 may perform a projection of the 3D graphical construct corresponding to the virtual landmark onto the 2D image. To the extent that a different image will thereafter be displayed, the control unit 12 will adjust the target location in the image coordinate system to match the different (new) image, performing at least motion compensation. Through the foregoing, poorly visible or invisible anatomical landmarks or target regions can be virtually shown on an image and used for at least navigation purposes by a user of the system.

Figure 7:
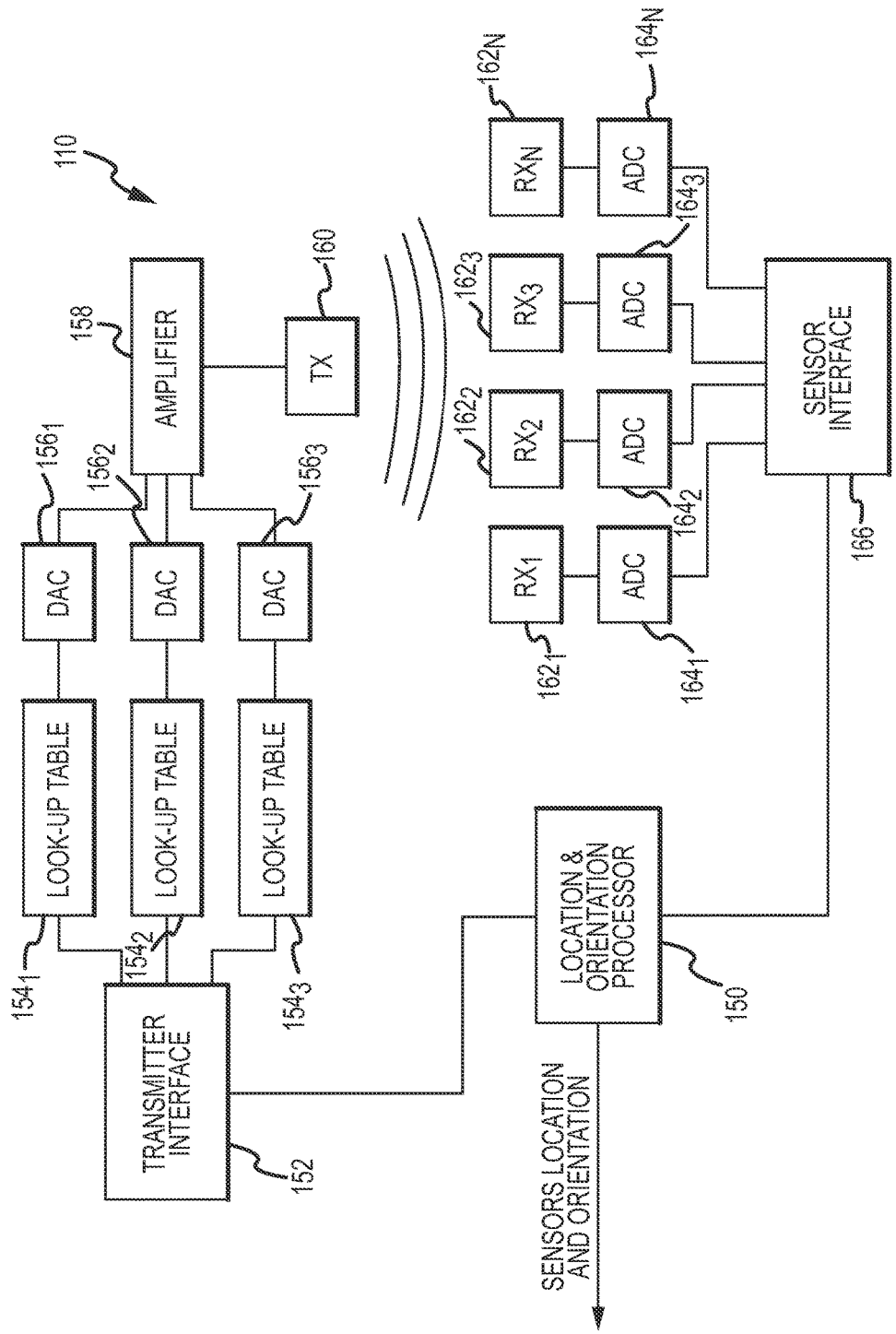
FIG. 7 is a schematic and block diagram of one exemplary embodiment of a medical positioning system (MPS).

FIG. 7 is a schematic and block diagram of one exemplary embodiment of MPS 20, designated as an MPS 108, as also seen by reference to U.S. Pat. No. 7,386,339, referred to above, and portions of which are reproduced below, which generally describes, at least in part, the gMPS™ medical positioning system commercially offered by MediGuide Ltd. It should be understood that variations are possible, for example, as also seen by reference to U.S. Pat. No. 6,233,476 entitled MEDICAL POSITIONING SYSTEM, also hereby incorporated by reference in its entirety. Another exemplary magnetic field-based MPS is the Carto™ system commercially available from Biosense Webster, and as generally shown and described in, for example, U.S. Pat. No. 6,498,944 entitled "Intrabody Measurement," and U.S. Pat. No. 6,788,967 entitled "Medical Diagnosis, Treatment and Imaging Systems," both of which are incorporated herein by reference in their entireties. Accordingly, the following description is exemplary only and not limiting in nature.

MPS system 110 includes a location and orientation processor 150, a transmitter interface 152, a plurality of look-up table units $154_1$, $154_2$ and $154_3$, a plurality of digital to analog converters (DAC) $156_1$, $156_2$ and $156_3$, an amplifier 158, a transmitter 160, a plurality of MPS sensors $162_1$, $162_2$, $162_3$ and $162_N$, a plurality of analog to digital converters (ADC) $164_1$, $164_2$, $164_3$ and $164_N$ and a sensor interface 166.

Transmitter interface 152 is connected to location and orientation processor 150 and to look-up table units $154_1$, $154_2$ and $154_3$. DAC units $156_1$, $156_2$ and $156_3$ are connected to a respective one of look-up table units $154_1$, $154_2$ and $154_3$ and to amplifier 158. Amplifier 158 is further connected to transmitter 160. Transmitter 160 is also marked TX. MPS sensors $162_1$, $162_2$, $162_3$ and $162_N$ are further marked $RX_1$, $RX_2$, $RX_3$ and $RX_N$, respectively. Analog to digital converters (ADC) $164_1$, $164_2$, $164_3$ and $164_N$ are respectively connected to sensors $162_1$, $162_2$, $162_3$ and $162_N$ and to sensor interface 166. Sensor interface 166 is further connected to location and orientation processor 150.

Each of look-up table units $154_1$, $154_2$ and $154_3$ produces a cyclic sequence of numbers and provides it to the respective DAC unit $156_1$, $156_2$ and $156_3$, which in turn translates it to a respective analog signal. Each of the analog signals is respective of a different spatial axis. In the present example, look-up table $154_1$ and DAC unit $156_1$ produce a signal for the X axis, look-up table $154_2$ and DAC unit $156_2$ produce a signal for the Y axis and look-up table $154_3$ and DAC unit $156_3$ produce a signal for the Z axis.

DAC units $156_1$, $156_2$ and $156_3$ provide their respective analog signals to amplifier 158, which amplifies and provides the amplified signals to transmitter 160. Transmitter 160 provides a multiple axis electromagnetic field, which can be detected by MPS sensors $162_1$, $162_2$, $162_3$ and $162_N$. Each of MPS sensors $162_1$, $162_2$, $162_3$ and $162_N$ detects an electromagnetic field, produces a respective electrical analog signal and provides it to the respective ADC unit $164_1$, $164_2$, $164_3$ and $164_N$ connected thereto. Each of the ADC units $164_1$, $164_2$, $164_3$ and $164_N$ digitizes the analog signal fed thereto, converts it to a sequence of numbers and provides it to sensor interface 166, which in turn provides it to location and orientation processor 150. Location and orientation processor 150 analyzes the received sequences of numbers, thereby determining the location and orientation of each of the MPS sensors $162_1$, $162_2$, $162_3$ and $162_N$. Location and orientation processor 150 further determines distortion events and updates look-up tables $154_1$, $154_2$ and $154_3$, accordingly.

It should be understood that the system 10, particularly control unit 12, as described above may include conventional processing apparatus known in the art (i.e., both hardware and/or software), including the capability of executing pre-programmed instructions stored in an associated memory, all performing in accordance with the functionality described herein. It is contemplated that the methods described herein, including without limitation the method steps of embodiments of the invention, may be programmed in a preferred embodiment, with the resulting software being stored in an associated memory and may also constitute the means for performing such methods. Implementation of embodiments, in software, in view of the foregoing enabling description, would require no more than routine application of programming skills by one of ordinary skill in the art. The system may further be of the type having both ROM, RAM, a combination of non-volatile and volatile (modifiable) memory so that the software can be stored and yet allow storage and processing of dynamically produced data and/or signals.

Although numerous embodiments of this invention have been described above with a certain degree of particularity, those skilled in the art could make numerous alterations to the disclosed embodiments without departing from the spirit or scope of this invention. All directional references (e.g., plus, minus, upper, lower, upward, downward, left, right, leftward, rightward, top, bottom, above, below, vertical, horizontal, clockwise, and counterclockwise) are only used for identification purposes to aid the reader's understanding of the present invention, and do not create limitations, particularly as to the position, orientation, or use of the invention. Joinder references (e.g., attached, coupled, connected, and the like) are to be construed broadly and may include intermediate members between a connection of elements and relative movement between elements. As such, joinder references do not necessarily infer that two elements are directly connected and in fixed relation to each other. It is intended that all matter contained in the above description or shown in the accompanying drawings shall be interpreted as illustrative only and not limiting. Changes in detail or structure may be made without departing from the spirit of the invention as defined in the appended claims.

What is claimed is:

1. An apparatus for superimposing a virtual landmark on an image of a region of interest in a patient's body, comprising:

a localization system configured to produce location readings with respect to points within said region of interest in accordance with an output of a location sensor disposed at a distal end of medical device as said distal end of said device moves within said region of interest, said location readings are associated with a three-dimensional location of said location sensor in a reference coordinate system, which is registered with an image coordinate system associated with said image; and a control unit having a user interface configured to receive a signal to record one of said location readings as a location input and associating the location input with the reference coordinate system, said location input corresponding to a desired point within said region of interest where said virtual landmark is to be established, said control unit being configured to superimpose a representation of said medical device distal end on said image, and wherein said recorded one location reading corresponds to the position of the representation of the medical device distal end on said image at a time when said one location reading was recorded, said control unit being configured to determine a target location in said image coordinate system corresponding to said recorded location input, said control unit being further configured to superimpose a representation of said virtual landmark on said image at said target location.

2. The apparatus of claim 1 wherein said control unit is further configured to (1) modify said recorded location input to compensate for motion at said desired point in said region of interest between a first time when said image was acquired and a second time when said location input was recorded; and (2) transform said motion-compensated location input from said reference coordinate system to said image coordinate system to thereby produce said target location.

3. The apparatus of claim 2 further including a patient reference sensor (PRS) coupled to said localization system configured for affixation to said patient and for providing a PRS location reading indicative of at least patient body movement, said control unit being further configured to record a PRS location reading with said virtual landmark-recorded location input, wherein said control unit is configured to further determine said motion-compensated location input in accordance with at least the recorded PRS location reading so as to compensate for said patient body movements.

4. The apparatus of claim 2 further including a patient reference sensor (PRS) coupled to said localization system configured for affixation to said patient and for providing a PRS location reading indicative of at least respiration-induced patient movements, said control unit being further configured to record a PRS location reading with said virtual landmark-recorded location input, wherein said control unit is configured to further determine said motion-compensated location input in accordance with at least the recorded PRS location reading so as to compensate for said respiration-induced patient movements.

5. A method of superimposing a virtual landmark on an image of a region of interest in a patient's body, comprising the steps of:

registering a reference coordinate system associated with a localization system with an image coordinate system wherein the localization system is configured to produce location readings with respect to points within the region of interest in accordance with the output of a location sensor at a distal end of a medical device as the distal end of the device moves within the region of interest wherein the location readings are associated with a three-dimensional location of the location sensor in the reference coordinate system;

receiving a signal to record a location reading in accordance with the output of the location sensor wherein a representation of the medical device distal end is superimposed on the image, and wherein the recorded location reading corresponds to the position of the representation of the medical device distal end on the image at a time when the location reading was recorded;

determining a target location in the image coordinate system based on the recorded location reading in the reference coordinate system; and superimposing a representation of the virtual landmark on the image at the target location.

6. The method of claim 5 further including the steps of:

modifying the recorded location reading to compensate for motion at the desired point in the region of interest between a first time when the image was acquired and a second time when the location reading was recorded; and transforming the motion-compensated location reading from the reference coordinate system to the image coordinate system to thereby produce the target location.

7. An apparatus for superimposing a virtual landmark on an image of a region of interest in a patient's body, comprising:

localization means for producing location readings with respect to points within said region of interest in accordance with an output of a location sensor disposed at a distal end of a medical device as said distal end of said device is moving within said region of interest wherein said location readings are associated with a three-dimensional location of said location sensor in reference coordinate system that is registered with an image coordinate system associated with said image; and control means for producing a user interface configured to receive a signal to record a location reading produced by the localization means in accordance with the output of said location sensor disposed in said medical device wherein said recorded location reading corresponds to a desired point within said region of interest where said virtual landmark is to be established, said control unit being configured to superimpose a representation of said medical device distal end on said image, and wherein said recorded location reading corresponds to the position of the representation of the medical device distal end on said image at a time when said location reading was recorded, said control means being further configured to modify said recorded location reading to compensate for motion at said desired point in said region of interest between a first time when said image was acquired and a second time when said location reading was recorded; said control means being further configured to transform said motion-compensated location reading from said reference coordinate system to said image coordinate system to thereby produce a target location in said image coordinate system corresponding to said recorded location reading, said control means being further configured to superimpose a representation of said virtual landmark on said image at said target location.

8. The apparatus of claim 7 further including a patient reference sensor (PRS) coupled to said localization means configured for affixation to said patient and for providing a PRS location reading indicative of patient body movement, said control means being further configured to record a PRS location reading with said virtual landmark-recorded location reading, wherein said control means is configured to further determine said motion-compensated location reading in accordance with at least the recorded PRS location reading so as to compensate for said patient body movements.

9. The apparatus of claim 1 wherein said medical device comprises a catheter, and wherein said location input corresponds to a distal catheter tip of the catheter, said location input corresponding to the desired point within said region of interest where said virtual landmark is to be established.

10. The apparatus of claim 2 further including an electrocardiogram (ECG) monitor configured to produce an ECG signal indicative of said patient's cardiac phase, said control unit being further configured to sample said ECG signal when said virtual landmark location input was recorded, wherein said control unit is configured to further determine said motion-compensated location input in accordance with at least the sampled ECG signal so as to compensate for heartbeat induced movement.

11. The apparatus of claim 10 wherein said control unit is configured to superimpose said representation of said virtual landmark on a sequence of images defining a cine-loop (CL) wherein each one of said sequence has a respective timing parameter associated therewith, said control unit being further configured to select one of said sequence of images based on said timing parameter and a then-prevailing sample of said ECG signal to thereby achieve ECG-synchronized playback of said image sequence.

12. The apparatus of claim 11 wherein said virtual landmark has a first position in said reference coordinate system corresponding to a first timing parameter value and a second position in said reference coordinate system corresponding to a second timing parameter value.

13. The apparatus of claim 1 further including a display coupled to said control unit, said user interface of said control unit being configured for:
 (i) presenting said image of said region of interest on said display; and
 (ii) receiving from a user a graphical input on said image indicating said virtual landmark.

14. The method of claim 6 further including the steps of:

recording a patient reference sensor (PRS) location reading from a PRS coupled to the localization system and configured for affixation to the patient indicative of patient body movements; and determining the motion-compensated location reading in accordance with at least the recorded PRS location reading so as to compensate for the patient body movements.

15. The method of claim 14 further including the steps of:

sampling an electrocardiogram (ECG) signal indicative of the patient's cardiac phase;

determining the motion-compensated location reading in accordance with at least the sampled ECG signal so as to compensate for heartbeat induced movement.

16. The method of claim 15 wherein said superimposing step includes the sub-steps of:

providing a sequence of images defining a cine-loop (CL) wherein each one of the sequence has a respective timing parameter associated therewith; and selecting one of the sequence of images based on the timing parameter and a then-prevailing sample of the ECG signal to thereby achieve ECG-synchronized playback of the cine-loop.

17. The method of claim 5 further including the steps of:
- presenting the image of the region of interest on a display; and
- receiving from a user a graphical input on the image indicating the location of the virtual landmark.

18. The apparatus of claim 8 further including an electrocardiogram (ECG) monitor configured to produce an ECG signal indicative of said patient's cardiac phase, said control means being further configured to sample said ECG signal when said virtual landmark location reading was recorded, wherein said control means is configured to further determine said motion-compensated location reading in accordance with at least the sampled ECG signal so as to compensate for heartbeat induced movement.

19. The apparatus of claim 18 wherein said control means is configured to superimpose said representation of said virtual landmark on a sequence of images defining a cine-loop (CL) wherein each one of said sequence has a respective timing parameter associated therewith, said control means being further configured to select one of said sequence of images based on said timing parameter and a then-prevailing sample of said ECG signal to thereby achieve ECG-synchronized playback of said image sequence.

20. The apparatus of claim 7 further including a display coupled to said control means, said control means producing said user interface so as to
- (i) present said image of said region of interest on said display; and
- (ii) receive from a user a graphical designation on said image indicating the location of said virtual landmark.

21. The apparatus of claim 7 wherein said virtual landmark has a first position in said reference coordinate system corresponding to a first timing parameter value and a second position in said reference coordinate system corresponding to a second timing parameter.

* * * * *